United States Patent
Byun et al.

(10) Patent No.: US 7,906,137 B2
(45) Date of Patent: Mar. 15, 2011

(54) DELIVERY AGENTS FOR ENHANCING MUCOSAL ABSORPTION OF THERAPEUTIC AGENTS

(75) Inventors: Youngro Byun, Kwangju (KR); Seulki Lee, Seoul (KR); Hyuntae Moon, Kwangju (KR)

(73) Assignee: Mediplex Corporation, Korea, Samsung-Dong, Kangnam-Ku, Seoul (KR)

( * ) Notice: Subject to any disclaimer, the term of this patent is extended or adjusted under 35 U.S.C. 154(b) by 2074 days.

(21) Appl. No.: 10/851,477

(22) Filed: May 21, 2004

(65) Prior Publication Data

US 2005/0260237 A1    Nov. 24, 2005

(51) Int. Cl.
*A61F 13/00* (2006.01)
*A61K 31/21* (2006.01)
*A61K 9/20* (2006.01)
*A01N 37/00* (2006.01)
*C07J 9/00* (2006.01)

(52) U.S. Cl. ......... 424/434; 424/464; 514/506; 514/510; 552/553

(58) Field of Classification Search .......... None
See application file for complete search history.

(56) References Cited

U.S. PATENT DOCUMENTS

| | | | |
|---|---|---|---|
| 5,541,348 A * | 7/1996 | Ayra et al. ............... | 552/506 |
| 6,251,428 B1 | 6/2001 | Yoo | |
| 6,395,713 B1 * | 5/2002 | Beigelman et al. ......... | 514/44 R |
| 6,458,383 B2 | 10/2002 | Chen et al. | |
| 6,461,643 B2 | 10/2002 | Milstein et al. | |
| 6,589,943 B2 * | 7/2003 | Byun et al. ............... | 514/56 |
| 6,589,946 B2 | 7/2003 | Gilat | |
| 6,627,228 B1 | 9/2003 | Milstein et al. | |
| 6,645,525 B1 | 11/2003 | Woiszwillo | |
| 6,936,591 B2 * | 8/2005 | Dumic et al. ............... | 514/29 |

FOREIGN PATENT DOCUMENTS

WO      WO 0135998 A1 *  5/2001

OTHER PUBLICATIONS

Singletary et al. (1972) Biochimica et Biophysica Acta 266:238-245.*
Bowe et al. (1997) Proceedings of the National Academy of Sciences USA 94:12218-12223.*
Excipient—(2007) in The American Heritage Dictionary of the English Language.*
Moses et al. Insulin administered intranasally as an insulin-bile salt aerosol:effectiveness and reproducibility in norml and diabetic subjects. Diabetes 1983 32:1040-1046.*
Scott-Moncrieff et al. Enhancement of intestinal insulin adsorption by bile salt-fatty acid mixed micelles in dogs. Journal of Pharmaceutical Sciences 1994 88:1465-1469.*
Mantle et al. Clinca Chimica Acta 1999 281:101-108.*

* cited by examiner

*Primary Examiner* — Juliet C Switzer
*Assistant Examiner* — Caralynne Helm
(74) *Attorney, Agent, or Firm* — Clayton, Howarth & Cannon, P.C.

(57)    ABSTRACT

A delivery agent for delivering a biologically active agent to a warm-blooded animal includes a hydrophobic moiety covalently bonded to a hydrophilic moiety. The hydrophobic moiety can include bile acids, sterols, or hydrophobic small molecules. The hydrophilic moiety can include α-amino acids, dipeptides or tripeptides, or hydrophilic small molecules. An illustrative delivery agent is $N^{\alpha}$-deoxycholyl-L-lysine-methylester. The delivery agent and the biologically active agent are mixed together to form a complex, which is then administered to the animal. These complexes are particularly useful for oral administration of biologically active agents, but other routes of administration may be used.

11 Claims, 6 Drawing Sheets

FIG. 2A
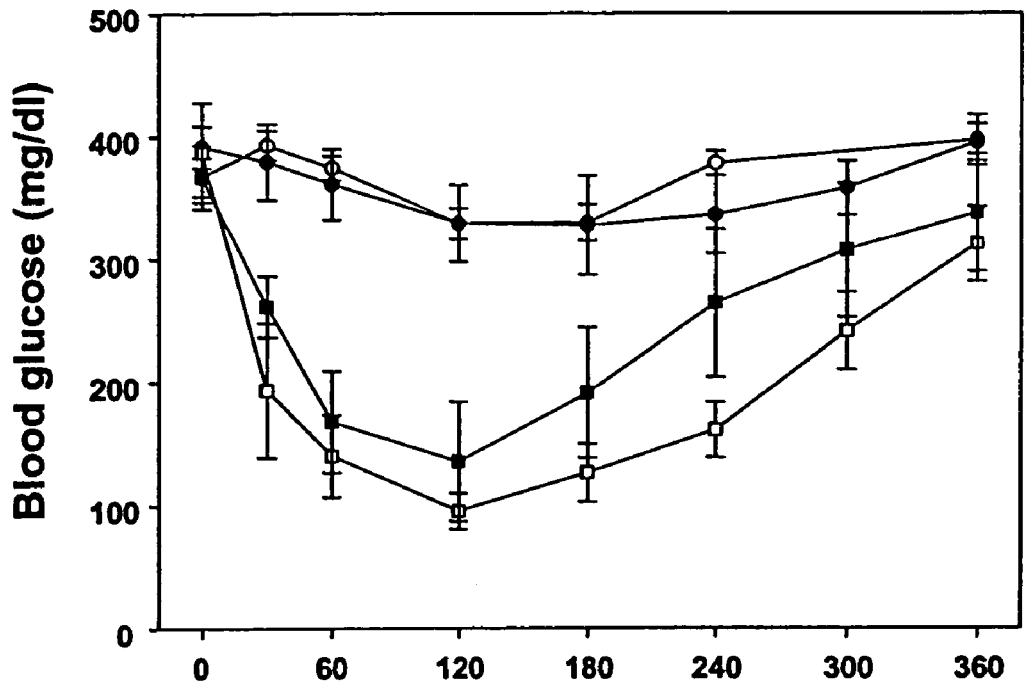
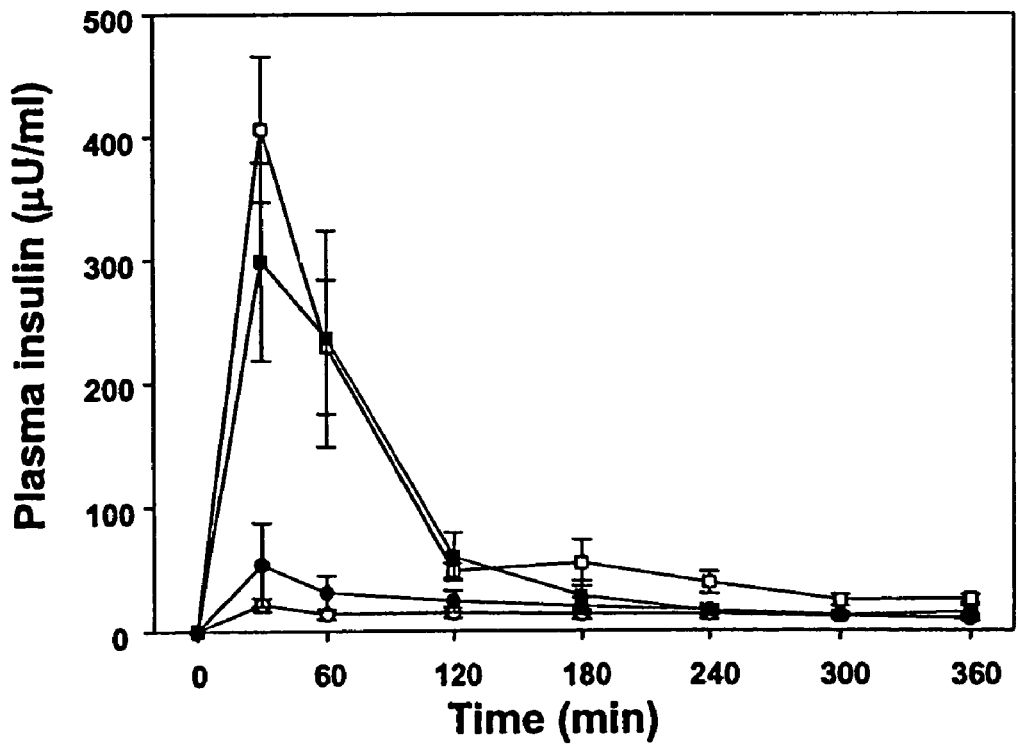
Fig. 2B

DELIVERY AGENTS FOR ENHANCING MUCOSAL ABSORPTION OF THERAPEUTIC AGENTS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to compositions for delivering biologically active agents, particularly therapeutic agents. The compositions comprise a synthetic delivery agent that facilitates oral delivery of the biologically active agent and that may also be used in connection with other routes of delivery. The invention also relates to methods for the preparation and administration of such compositions.

Conventional means for delivering biologically active agents are often severely limited by biological, chemical, and physical barriers. Typically, these barriers are imposed by the environment through which delivery occurs, the environment of the target for delivery, or the target itself. Biologically active agents are particularly vulnerable to such barriers. In the delivery of therapeutic agents, barriers are imposed by the body. Physical barriers, such as the skin and various organ membranes, are relatively impermeable to certain active agents, but must be traversed before reaching a target, such as the circulatory system.

Oral delivery would be the route of choice for administering many biologically active agents to animals, including humans, but for barriers that interfere with efficient absorption of these agents. Among the numerous agents that are not typically amenable to oral administration are biologically active peptides, such as insulin, calcitonin, growth hormone, and glucagon-like-peptide-1; polysaccharides and mucopolysaccharides including, but not limited to, heparin and heparinoids; antibiotics; and other organic substance. These agents may be rendered ineffective or may be destroyed in the gastrointestinal (GI) tract by acid hydrolysis, enzymes, electrostatic charges, or the like, or may simply not be absorbed.

Many delivery agents are fairly hydrophobic, whereas many bioactive agents are hydrophilic. This difference in solubility characteristics between the delivery agent and the bioactive agent can be problematic in designing commercially acceptable dosage formulations that exhibit biological activity in vivo. Thus, the ability to tailor the solubility of the delivery agent to the solubility of the bioactive agent would increase bioavailability of the bioactive agent.

Due to the hydrophilicity of many bioactive agents, such bioactive agents typically exhibit low bioavailability. Chemical modification of a native bioactive agent can result in an increase of lipophilicity, however, such modification imposes high costs for preparing and purifying the final product. If a delivery agent could increase lipophilicity of a native bioactive agent by simple mixing with the bioactive agent, it would allow increased bioavailiability and would also provide simplicity of preparation and low cost.

During oral delivery, a significant amount of delivery agent may precipitate under physiological conditions. The precipitated delivery agent is then unavailable for delivery of the bioactive agent to a point further along the GI tract and is also potentially toxic. Reducing the dose of delivery agent would allow more effective delivery of the bioactive agent with a low concentration of delivery agent and less toxicity.

Typical delivery agents do not interact with bioactive agents under physiological conditions. This is why a significant amount of delivery agent and/or enhancer are usually needed to deliver the bioactive agent. Increasing the ability of a delivery agent to interact with a bioactive agent would allow more effective delivery at much lower concentrations of delivery agent.

Maintaining or controlling the effective charge of a bioactive agent is crucial for increasing permeability of a bioactive agent through membranes. If a delivery agent could control the net charge of a bioactive agent by simple mixing of the delivery agent and the bioactive agent, it would allow more effective delivery of the bioactive agent.

The stability of a bioactive agent to proteolysis in the GI tract or at tissue surfaces can be a significant contributing factor for delivery efficiency. If a delivery agent could increase the stability of a bioactive agent toward proteolysis, it would allow more effective delivery.

A high aggregation state of a bioactive agent (especially for peptide and proteins drugs) results in low bioavailability after oral administration. If a delivery agent could alter the aggregation state of a bioactive agent, it would allow more effective delivery.

In view of the foregoing, it will be appreciated that providing compositions and methods for delivery of bioactive agents, wherein degradation and inactivation are inhibited, solubility problems are reduced, interaction of bioactive agents and delivery agents is increased, electrostatic charge is controlled, lipophilicity of bioactive agents is increased, and aggregation state of bioactive agents is altered, would be a significant advancement in the art.

BRIEF SUMMARY OF THE INVENTION

It is a feature of the present invention to provide compositions and methods for delivery of bioactive agents wherein degradation and inactivation of the bioactive agents are inhibited.

It is also a feature of the present invention to provide compositions and methods for delivery of bioactive agents wherein solubility problems are reduced and interaction of bioactive agents and delivery agents is increased.

It is another feature of the present invention to provide compositions and method for delivery of bioactive agents wherein electrostatic charge of the bioactive agents can be controlled.

It is still another feature of the present invention to provide compositions and methods for delivery of bioactive agents wherein lipophilicity of the bioactive agents is increased.

It is yet another feature of the present invention to provide compositions and methods for delivery of bioactive agents wherein the aggregation state of bioactive agents can be altered.

These and other objects can be addressed by providing a delivery agent for delivery of a biologically active agent to a warm-blooded animal, the delivery agent comprising (a) a hydrophobic moiety selected from the group consisting of bile acids, sterols, derivatives of such bile acids and sterols, and small hydrophobic molecules having molecular weights of less than about 500 daltons and (b) a hydrophilic moiety covalently bonded to the hydrophobic moiety, wherein the hydrophilic moiety is positively charged, negatively charged, or a salt.

Illustrative hydrophilic moieties according to the present invention include α-amino acids, such as lysine, arginine, histidine, aspartic acid, or glutamic acid; dipeptides or tripeptides; and hydrophilic small molecules having a molecular weight of about 100 to about 3000. Illustratively, the delivery agent has a molecular weight of about 400 to about 4000 daltons. $N^\alpha$-deoxycholyl-L-lysine-methylester is an illustrative delivery agent according to the present invention.

Another illustrative embodiment of the invention comprises a composition comprising a mixture of a biologically active agent and a delivery agent, wherein the delivery agent comprises (a) a hydrophobic moiety selected from the group consisting of bile acids, sterols, derivatives of such bile acids and sterols, and small hydrophobic molecules having a molecular weight of less than about 500 daltons and (b) a hydrophilic moiety covalently bonded to the hydrophobic moiety, wherein the hydrophilic moiety is positively charged, negatively charged, or a salt thereof.

Illustrative biologically active agents according to the present invention include human growth hormone, recombinant human growth hormone, bovine growth hormone, porcine growth hormone, growth hormone-releasing hormone, alpha-interferon, beta-interferon, gamma-interferon, interleukin-1, interleukin-2, insulin, porcine insulin, bovine insulin, human insulin, human recombinant insulin, insulin-like growth factor (IGF), insulin-like growth factor-1 (IGF-1), glucagon-like peptide-1 (GLP-1), heparin, unfractionated heparin, heparinoids, dermatans, chondroitins, low molecular weight heparin, pentasaccharide, calcitonin, salmon calcitonin, eel calcitonin, human calcitonin, erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thromboprotein, fugrastim, prostaglandins, cyclosporin, vasopressin, cromolyn sodium, sodium chromoglycate, disodium chromoglycate, vancomycin, parathyroid hormone, fragments of parathyroid hormone, desferrioxamine, antimicrobial agents, antifungal agents, and vitamins; analogs, fragments, mimetics, and polyethylene glycol-modified derivatives thereof; and mixtures thereof. Insulin, low molecular weight heparin, and calcitonin are especially illustrative of biologically active agents that can be delivered according to the present invention. Excipients, diluents, disintegrants, lubricants, plasticizers, colorants, and mixtures thereof can also be added to the present compositions.

Another illustrative embodiment of the invention comprises a dosage form for delivery of a biologically active agent to a warm-blooded animal, the dosage form comprising a mixture of the biologically active agent and a delivery agent, wherein the delivery agent comprises (a) a hydrophobic moiety selected from the group consisting of bile acids, sterols, derivatives of such bile acids and sterols, and small hydrophobic molecules having a molecular weight of less than about 500 daltons and (b) a hydrophilic moiety covalently bonded to the hydrophobic moiety, wherein the hydrophilic moiety is positively charged, negatively charged, or a salt thereof. The dosage forms can comprise a tablet, a capsule, a powder, a liquid, or an emulsion.

Still another illustrative embodiment of the invention comprises a method for administering a biologically active agent to a warm-blooded animal, the method comprising administering a composition comprising a mixture of the biologically active agent and a delivery agent, wherein the delivery agent comprises (a) a hydrophobic moiety selected from the group consisting of bile acids, sterols, derivatives of such bile acids and sterols, and small hydrophobic molecules having a molecular weight of less than about 500 daltons and (b) a hydrophilic moiety covalently bonded to the hydrophobic moiety, wherein the hydrophilic moiety is positively charged, negatively charged, or a salt thereof.

Oral and intra-jeju-ileum administration are illustrative routes of administration according to this method.

BRIEF DESCRIPTION OF THE SEVERAL VIEWS OF THE DRAWINGS

FIGS. 2A and 2B show effects of $N^\alpha$-deoxycholyl-L-lysine-methylester/insulin complexes on blood glucose levels (FIG. 2A; measured by ONETOUCH® glucose monitoring card) and plasma insulin levels (FIG. 2B; measured by insulin RIA assay) at various times after oral administration to streptozocin-induced, overnight-fasted Type I diabetic rats: 42 U/kg human insulin (○); 42 U/kg human insulin+0.75 mg/kg $N^\alpha$-deoxycholyl-L-lysine-methylester (●); 42 U/kg human insulin+1.5 mg/kg $N^\alpha$-deoxycholyl-L-lysine-methylester (■); 42 U/kg human insulin+3.0 mg/kg $N^\alpha$-deoxycholyl-L-lysine-methylester (□).

DETAILED DESCRIPTION

Figure 1:
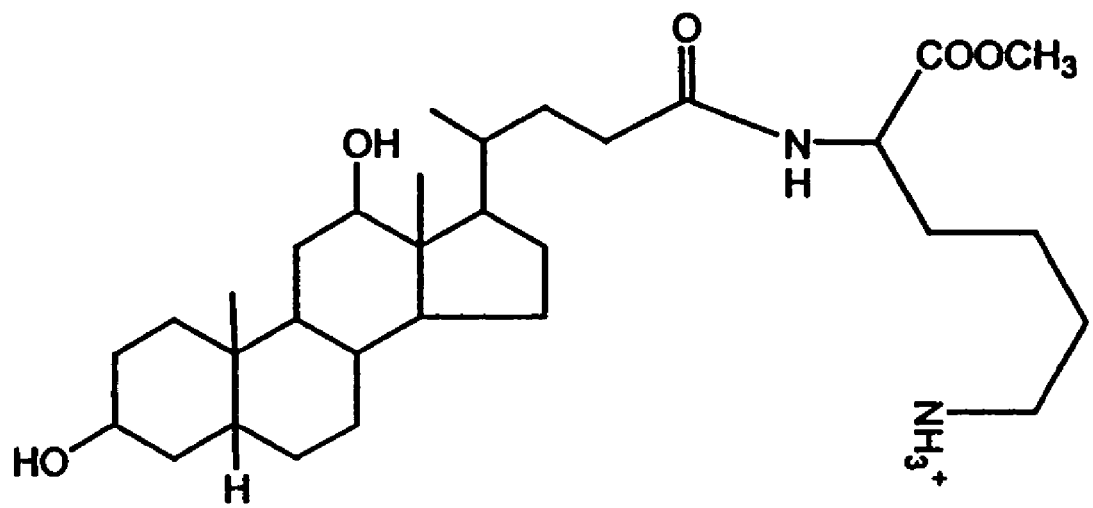
FIG. 1. shows a representation of $N^\alpha$-deoxycholyl-L-lysine-methylester.

Before the present compositions and methods for delivery of therapeutic agents are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a dosage form comprising a biologically active agent" includes reference to a dosage form comprising two or more of such biologically active agents, reference to "an α-amino acid" includes reference to two or more of such α-amino acids, and reference to "the positively charged group" includes reference to two or more of such positively charged groups.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "bile acids" means natural and synthetic derivatives of the steroid, cholanic acid, including, without limitation, cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid.

As used herein, "sterols" means alcohols structurally related to the steroids including, without limitation, cholestanol, coprostanol, cholesterol, epicholesterol, ergosterol, and ergocalciferol.

As used herein, "modified peptide" means a synthetic dipeptide or tripeptide that contains positively or negatively charged functional groups that may induce electrostatic interaction within an active agent and also increase solubility of the delivery agent. Protecting groups may be used to avoid unwanted side reactions, as would be known to those skilled in the art, and also to increase efficiency of delivery of the therapeutic agent. Esters of peptides, and the like, are also considered modified peptides.

As used herein, "small chemicals" or "small molecules" means chemicals having a molecular weight of about 100 to about 3000 and that contain charged functional groups with appropriate salts.

As used herein, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals and, more particularly, in humans.

As used herein, "effective amount" means an amount of a drug or pharmacologically active agent that is nontoxic but sufficient to provide the desired local or systemic effect and performance at a reasonable benefit/risk ratio attending any medical treatment.

As used herein, "diluents" are inert substances added to increase the bulk of the formulation to make a tablet a practical size for compression. Commonly used diluents include calcium phosphate, calcium sulfate, lactose, kaolin, mannitol, sodium chloride, dry starch, powdered sugar, silica, and the like.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Typical amounts of lubricants range from about 0.1% by weight to about 5% by weight.

As used herein, "coloring agents" or "colorants" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" are agents for masking the objectionable taste of therapeutic agents. Flavoring agents vary considerably in their chemical structure, ranging from simple esters, alcohols, and aldehydes to carbohydrates and complex volatile oils. Synthetic flavors of almost any desired type are now available.

Biologically active agents suitable for use in the present invention include, but are not limited to, proteins, polypeptides, peptides, hormones, polysaccharides, and mucopolysaccharides and mixtures thereof, carbohydrates, lipids, other organic compounds, and particularly compounds that by themselves do not pass through the gastrointestinal mucosa and/or are susceptible to chemical and/or enzymatic cleavage by acids and enzymes in the gastro-intestinal tract, or any combination thereof.

Further examples of biologically active agents include, but are not limited to, the following, including synthetic, natural or recombinant sources thereof: growth hormones, including human growth hormones (hGH), recombinant human growth hormone (rhGH), bovine growth hormones, and porcine growth hormones; growth hormone-releasing hormones; interferons, including alpha-, beta-, and gamma-interferons; interleukin-1; interleukin-2; insulin, including porcine, bovine, human, and human recombinant insulins, optionally comprising counter ions such as sodium, zinc, calcium, and ammonium ions; insulin-like growth factor, including IGF-1; heparin, including unfractionated heparin, heparinoids, dermatans, chondroitins, low molecular weight heparin, very low molecular weight heparin, and ultra low molecular weight heparin including penta-saccharide; calcitonin, including salmon, eel, and human calcitonins; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferroxamine (DFO); parathyroid hormone (PTH), including its fragments; antimicrobials, including anti-fungal agents; vitamins; analogs, fragments, mimetics; or poly(ethylene glycol)-conjugated (Pegylated) versions of any of the above therapeutic agents.

An illustrative delivery agent according to the present invention comprises a hydrophobic moiety covalently coupled to a hydrophilic moiety. The hydrophobic moiety comprises a bile acid residue, a sterol residue, or a hydrophobic small molecule. The hydrophobic moiety (a) increases lipophilicity of the therapeutically active agent after ionic bonding of the delivery agent and the therapeutically active agent, thereby forming a complex, (b) assists in forming a particulate structure of the complex by providing the hydrophobic portion of the complex, (c) deaggregates highly aggregated protein forms, and (d) may be recognized by certain transporters, such as a bile acid transporter, thus facilitating absorption of the complexes. The hydrophilic moiety comprises, without restriction, modified peptides, small charged molecules, spermidine derivatives, and chelating agents, such as ethylenediaminetetraacetic acid (EDTA) and diethylenetriaminepentaacetic acid (DTPA). The hydrophilic moiety can be positively charged, negatively charged, and/or zwitterionic. The hydrophilic moiety provides the charged portion of the delivery agent, thereby providing for electrostatic interaction with the therapeutically active agent, (b) increasing solubility of the delivery agent by forming salt forms, and (c) being recognized by certain transporters, such as di- and tri-peptide transporters, thus facilitating absorption of the complexes.

Modified peptides may be recognized by di- and tri-peptide transporters (PEPT1 and PEPT2), which may mediate the efficient absorption of a wide variety of oral peptide-like drugs in the small intestine.

Delivery agents prepared by conjugation of a bile acid and a modified peptide may be recognized by a peptide transporter and also by a bile acid transporter, which may mediate the efficient absorption of a wide variety of delivery agent/biologically active agent complexes in the gastrointestinal (GI) membrane.

An illustrative cationic delivery agent according to the present invention is water soluble and positively charged. Examples of cationic delivery agents that can be used in the invention include, but are not limited to, agents having the formula

X—Y—R wherein X is the hydrophobic moiety comprising a bile acid or sterol residue or a small hydrophobic molecule having a molecular weight of less than about 500 daltons, Y is the hydrophilic moiety comprising a positively charged molecule, for example, without limitation, positively charged α-amino acids (Lys, Arg, and His); di- or tri-peptides that contain Lys, Arg, or His; polyamines, such as spermidine and spermine; and positively charged alkyl chain derivatives; or any combination thereof, wherein the positive charge is provided by an appropriate functional group, such as primary, secondary, tertiary, and/or quaternary amines with an appropriate salt, and R is the appropriate functional group, for example, without limitation, —OCH$_3$, —OCH$_2$CH$_3$, —OH, —O$^-$Na$^+$, —SO$_3^-$, or NH$_2$ with an appropriate salt.

An illustrative anionic delivery agent according to the present invention is water soluble and negatively charged. Examples of anionic delivery agents that can be used in the invention include, but are not limited to, agents having the formula

X—Y'—R wherein X is the hydrophobic moiety comprising a bile acid or sterol residue or a small hydrophobic molecule having a molecular weight of less than about 500 daltons, Y' is the hydrophilic moiety comprising a negatively charged molecule, for example, without limitation, negatively charged α-amino acids (Glu and Asp); di- or tri-peptides that contain Glu or Asp; negatively charged chelating agents, such as DTPA or EDTA; or any combination thereof, wherein the negative charge is provided by an appropriate functional group, such as —COOH or —SO$_3^-$ with an appropriate salt, and R is an appropriate functional group, for example, without limitation, —OCH$_3$, —OCH$_2$CH$_3$, —OH, —O$^-$Na$^+$, —SO$_3^-$, or NH$_2$.

The delivery agents are made by conjugating the hydrophobic and hydrophilic moieties to each other. For example, either the hydrophobic moiety or the hydrophilic moiety can be activated and then reacted to the other moiety. An illustrative example of such a strategy is forming a succinimido derivative of a bile acid and then reacting the activated bile acid with an amine group of an α-amino acid, dipeptide, or tripeptide to form the conjugate. Another illustrative example of activating a hydrophilic moiety or hydrophobic moiety is activating a carboxylic acid group with thionyl chloride to form an acid chloride and then reacting the acid chloride with reactive amines, alcohols, thiols, Grignard reagents, and the like to form amide, ester, thioester, ketone, or other bonds linking the conjugate. In a similar manner, sulfonic acid groups can also be activated with thionyl chloride to form sulfonyl chloride groups, which can then be reacted with amines, alcohols, and the like to form sulfonamide, sulfonate ester, or other bonds. U.S. Pat. No. 5,618,433 describes formation of such bonds. Either the hydrophobic moiety or the hydrophilic moiety may be adapted to contain reactive —NH$_2$, —OH, —SH, or MgX moieties according to methods well known in the art to facilitate bonding of the hydrophobic moiety to the hydrophilic moiety. Still further, linkers, such as heterobifunctional linkers, may be used to conjugate the hydrophobic and hydrophilic moieties to each other. Such linkers are well known in the art and are commercially available.

Formulations

The compositions of the present invention may include one or more bioactive agents. In one illustrative embodiment, the delivery agents of the present invention may be used by simply mixing them with the selected bioactive agent prior to administration. Such mixtures may be prepared by mixing an aqueous solution of the delivery agent with an aqueous solution of the active ingredient, just prior to administration.

Alternatively, the delivery agent and the bioactive agent can be admixed during the formulation process. The solutions may optionally contain pharmaceutically acceptable additives.

Stabilizing additives may be incorporated into the delivery agent solution. With some active agents, the presence of such additives promotes the stability and dispersibility of the agent in solution. The stabilizing additives may be used at a concentration ranging between about 0.1 and 50% (w/v), illustratively about 1% (w/v). Suitable, but non-limiting, examples of stabilizing additives include propylene glycol, Tween™ surfactants, gelatin, methyl cellulose, polyethylene glycol, and organic solvents such as dimethylsulfoxide (DMSO), alcohols, carboxylic acids, and salts thereof.

The amount of bioactive agent used in a dose is an amount effective to accomplish the purpose of the particular bioactive agent. Such an effective amount can readily be determined by a person skilled in the art. The amount in the composition typically is a pharmacologically or biologically effective amount. However, the amount can be less than a pharmacologically or biologically effective amount when the composition is used in a dosage unit form, such as a solid, a capsule, a tablet, or a powder, an emulsion, or a liquid, because the dosage unit form may contain a multiplicity of delivery agent or bioactive agent compositions or may contain a divided pharmacologically or biologically effective amount. The total effective amounts can then be administered in cumulative units containing, in total, pharmacologically or biologically active amounts of biologically or pharmacologically active agent.

The total amount of bioactive agent to be used can be determined by those skilled in the art. However, because the presently disclosed delivery agents provide efficient delivery, lower amounts of biologically active agent than those used in prior dosage unit forms or delivery systems may be administered to the subject, while still achieving the same blood levels and biological effects.

The amount of delivery agent in the present composition is an amount effective for delivery of a selected bioactive agent, which can be determined without under experimentation for any particular delivery agent or bioactive agent by methods known to those skilled in the art. Thus, the amount of delivery agent in a composition according to the present invention will be an amount effective for delivery of the bioactive agent by the selected route of delivery.

Dosage unit forms can also include excipients, diluents, disintegrants, lubricants, coloring agents, flavoring agents, and mixtures thereof.

Administration of the present compositions or dosage unit forms preferably is oral, intracolonic, or intraduodenal. Particularly, the compositions of the present invention are useful in orally administering active agents, especially those that are not ordinarily orally deliverable.

The delivery compositions of the present invention may also include one or more enzyme inhibitors. Such enzyme inhibitors include, but are not limited to, compounds such as actinonin, H. Umezawa et al., Production of actinonin, an inhibitor of aminopeptidase M, by actinomycetes, 38 J. Antibiot. (Tokyo) 1629-1630 (1985), or epiactinonin and derivatives thereof.

The compositions of the subject invention are useful for administering biologically active agents to animals, including humans. The system is particularly advantageous for delivering biologically active agents that would otherwise be destroyed or rendered less effective by conditions encountered before the bioactive agent has reached its target zone (i.e. the area in which the bioactive agent of the delivery composition are to be released) and within the body of the animal to which they are administered.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Preparation of $N^\alpha$-deoxychoyl-L-lysine-methylester

Deoxycholic acid (200 mg, 0.5 mmol) and N-hydroxysuccinimide (76 mg, 0.67 mmol) were dissolved in anhydrous terahydrofuran (20 ml). To this solution, 1,3-dicyclohexylcarbodiimide (136 mg, 0.67 mmol) was added and stirred at 4° C. for 6 h. Urea derivatives were removed by filtration, the filtrate was poured into cold n-hexane (120 ml), and precipitates were dried under reduced pressure. The resulting succinimidodeoxycholate (230 mg, 0.48 mmol) was then reacted with the primary amine group of $N^\epsilon$-tBOC-Lys-OCH$_3$ (150 mg, 0.58 mmol) in dimethyformamide (10 ml) containing triethyl amine (200 µl, 1.7 mmol) for 12 h at room temperature. After reaction, the mixture was diluted with ethylacetate (30 ml) and successively washed with 10 ml of 0.5 N HCl, distilled water, 0.5 N NaOH, and distilled water. The organic phase was dried against magnesium sulfate and evaporated to dryness. The protected $\epsilon$-amine group of the lysine residue was deprotected by mixing with trifluoroacetic acid/dichloromethane (50/50, v/v) for 2 h at room temperature. The reaction volume was minimized by evaporation under reduced pressure, and the product was precipitated against cold diethyl ether and dried under reduced pressure. The dried product was then dissolved in distilled water and purified through a Sep-Pak® C18 column (Waters, Milford, Mass.). Finally, purified $N^\alpha$-deoxychoyl-L-lysine-methylester (DCK; FIG. 1) was lyophilized and obtained as a white powder.

EXAMPLE 2

In Vivo Evaluation of Delivery Agent/Insulin for Oral Formulation

An oral insulin formulation was prepared by mixing of human insulin and an illustrative delivery agent according to the present invention, i.e., $N^\alpha$-deoxychoyl-L-lysine-methylester, which was prepared according to the procedure of Example 1. Zinc human insulin was dissolved in a small volume of 5 mmol/l HCl and diluted with PBS (10 mM, pH 7.4) to a final concentration 42 U/ml as a stock solution. The delivery agent was dissolved in PBS (1.5 mg/ml). Insulin complexes were prepared by addition of a predetermined dose of delivery agent solution to insulin solution while vortexing. Insulin complexes were then orally administered to rats in liquid form using a gavage needle.

Female Sprague-Dawley rats (230~250 g) were housed in stainless steel metabolic cages and fed with rodent chow. After an initial 3-day acclimation period, the rats were fasted for 12 h before inducing diabetes mellitus. Streptozotocin (STZ) solution (60 mg/ml) was freshly prepared in acetate buffer (pH 4.5) and used within 1 h. After the baseline blood glucose level was determined, rats were injected intraperitoneally (i.p.) with STZ at 60 mg/kg. Five days after STZ treatment, rats with a fasted plasma glucose level greater than 300 mg/dl were selected as diabetic rats for further investigations.

The diabetic rats were fasted overnight for 12 h and then were orally administered insulin, insulin with delivery agent, or placebo (PBS) in PBS solution (10 mM, pH 7.4) using a gavage needle. Each group was randomized based on their average body weights and fasting blood glucose levels. The insulin dose was fixed (42 U/kg, equivalent to 1.5 mg/kg), but the amount of delivery agent ranged varied among 0.75, 1.5 and 3 mg/kg. The treated rats were kept in metabolic cages, with free access to water only. Blood samples were collected from the ocular orbital at predetermined time points (0, 30, 60, 120, 180, 240, 300, and 360 min). The blood glucose levels were determined immediately from fresh samples using a ONETOUCH® blood glucose monitoring system, and the hypoglycemic effect was expressed as mg/dl (FIG. 2A). Plasma insulin was measured by a Coat-A-Tube™ human insulin RIA kit (Diagnostic Products, Los Angeles, Calif.) according to the supplier's instructions, and results were expressed as µU/ml (FIG. 2B). These results show that a delivery agent according to the present invention increases plasma insulin levels and, correspondingly, decreases blood glucose levels as compared to controls when orally administered together with the biologically active agent.

Figure 3:
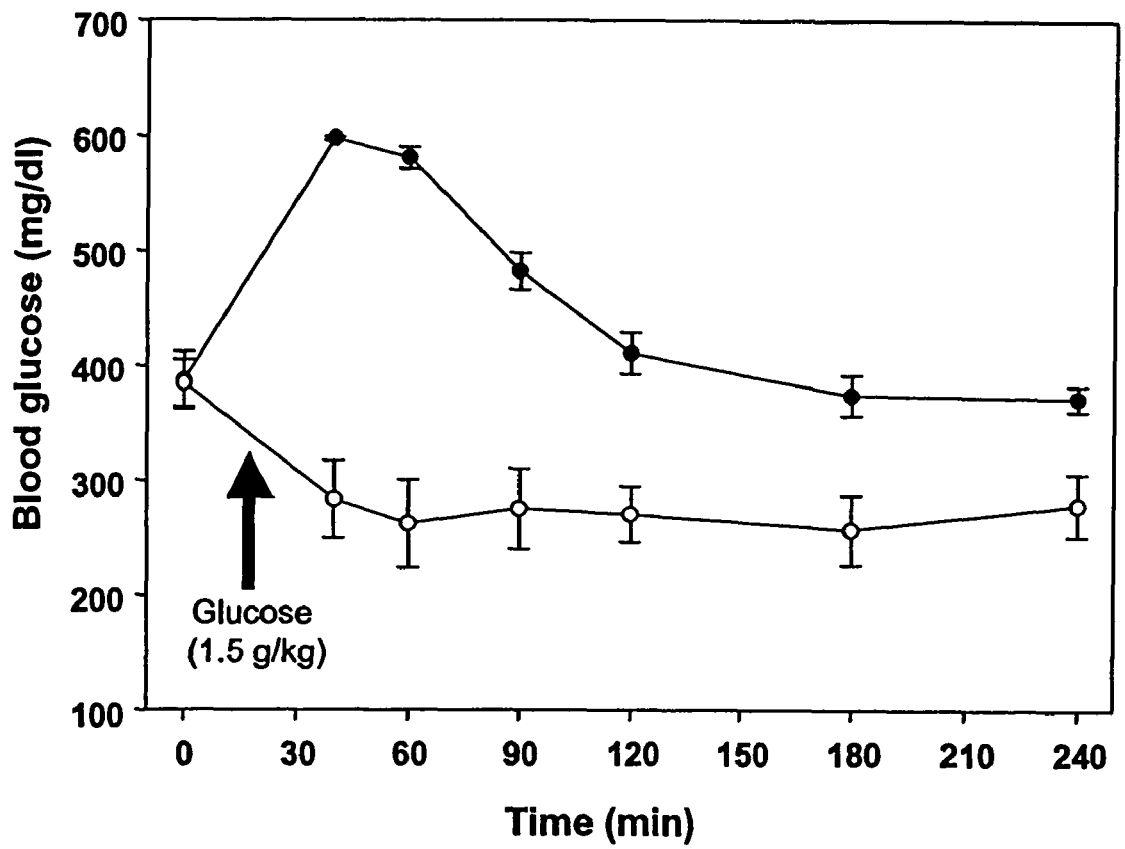
FIG. 3 shows the effect of $N^\alpha$-deoxycholyl-L-lysine-methylester/insulin complex on blood glucose levels at various times before and after administration of 1.5 g/kg of glucose (arrow) in an oral glucose tolerance test (OGTT): 42 U/kg human insulin in PBS (●); 42 U/kg human insulin+1.5 mg/kg $N^\alpha$-deoxycholyl-L-lysine-methylester (○).

Two different overnight-fasted diabetic rat groups (placebo and oral insulin) were randomized. At dose time 0 minutes, placebo (PBS) and oral insulin (42 U/kg of insulin in 1.5 mg/kg of delivery agent in PBS) were orally administered using a gavage needle. At dose time 20 minutes, 1.5 g/kg of glucose solution in PBS was orally administered to each group. Blood samples were collected and blood glucose was determined at 0, 40, 60, 90, 120, 180 and 240 min as described. The results of this test are illustrated in FIG. 3. These results show that co-administration of a delivery agent according to the present invention together with insulin results in a decreased blood glucose level as compared to administration of insulin without the delivery agent.

EXAMPLE 3

Stability Towards Proteolysis

Figure 4:
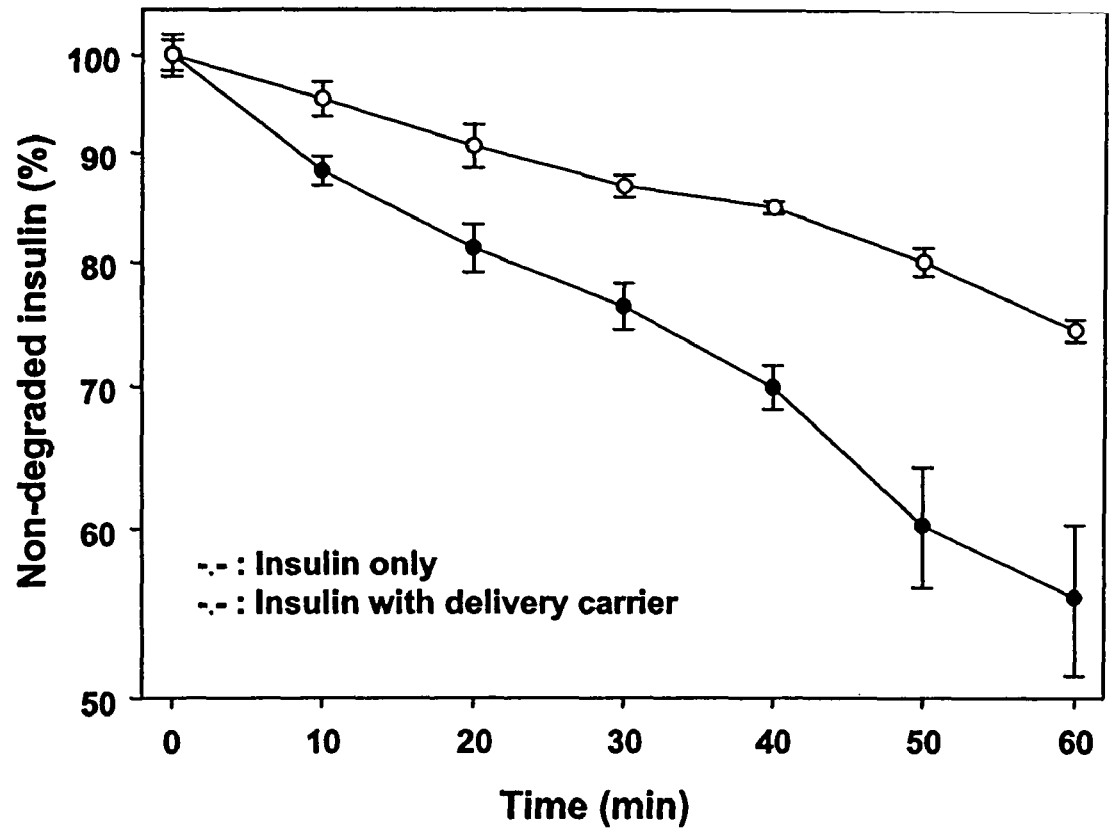
FIG. 4 shows stability of $N^\alpha$-deoxycholyl-L-lysine-methylester/insulin (○) toward enzymatic degradation in comparison with native insulin (●).

Insulin (100 µl, 1 mg/ml) and an equivalent amount of insulin/DCK (1:1, w/w) mixture were prepared in HEPES buffer (50 mmol/l; pH 7.4). Then, α-chymotrypsin (10 µl, 150 µg/ml) was added and the solutions were incubated at 37° C. At the indicated time points, aliquots were acidified with 890 µl of 0.1% trifluoroacetic acid. Each sample (containing 100 µg of protein at t=0) was analyzed by reversed-phase high performance liquid chromatography (HPLC, Shimadzu, Tokyo, Japan) on a C18 Bondapak® column (Waters Associates, Milford, Mass., USA) with a linear gradient of 5%-60% solvent B (solvent A: 0.1% trifluoroacetic acid; solvent B: 0.1% trifluoroacetic acid in 95% acetonitrile) over 55 min. The protein peak area at t=0 was designated as 100%. The results of the test are illustrated in FIG. 4. These results show that mixture of a delivery agent according to the present invention with insulin protects the insulin from proteolytic degradation as compared to a control lacking the delivery agent.

EXAMPLE 4

Dissociation of High Order Protein Aggregates

Figure 5:
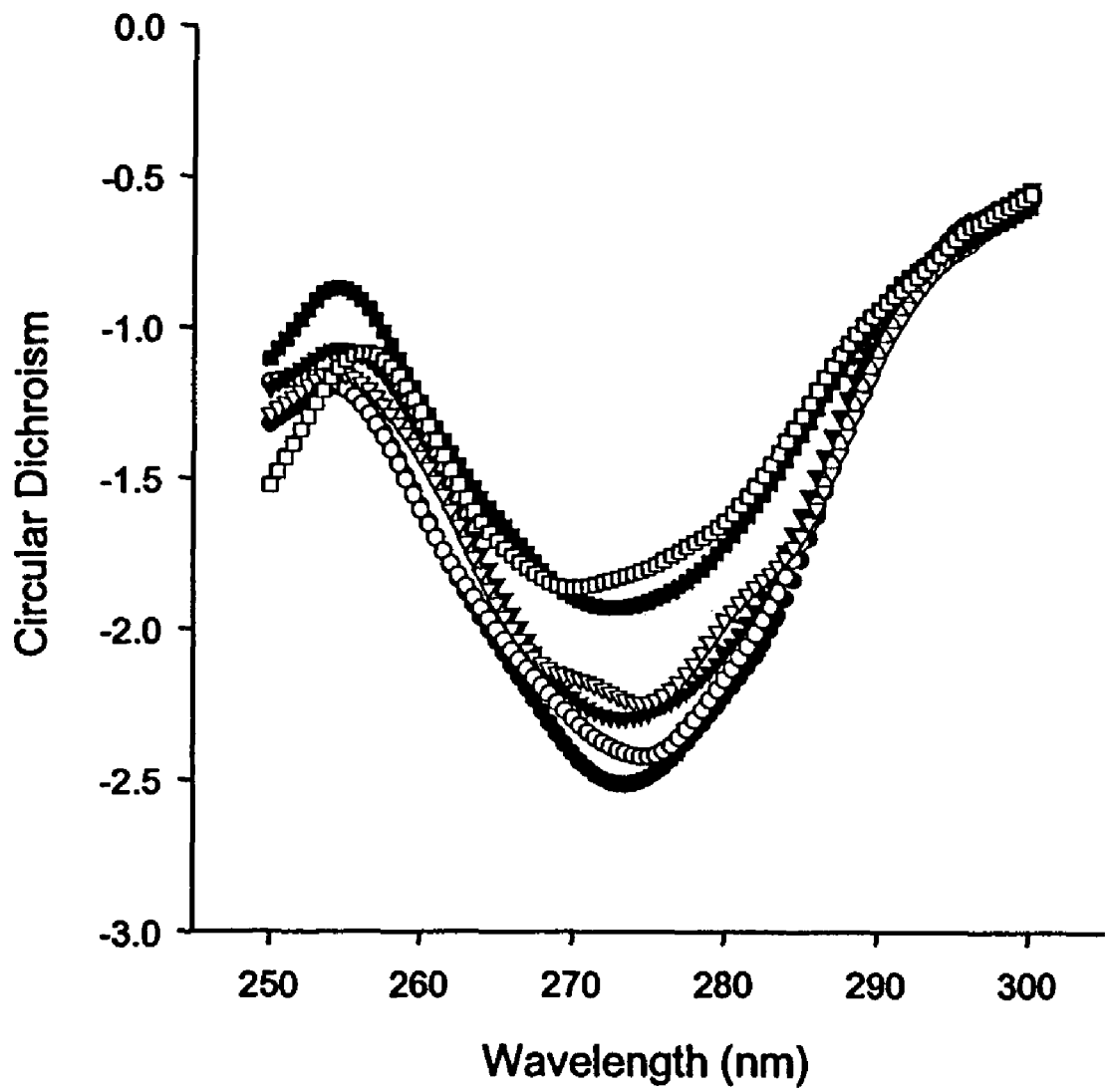
FIG. 5 shows change of aggregation state of insulin by increasing dose of delivery carrier, $N^\alpha$-deoxycholyl-L-lysine-methylester: 0.18 mM insulin (●); 0.18 mM insulin+0.18 mM $N^\alpha$-deoxychoyl-L-lysine-methylester (○); 0.18 mM insulin+0.37 mM $N^\alpha$-deoxycholyl-L-lysine-methylester (▼); 0.18 mM insulin+0.55 mM $N^\alpha$-deoxycholyl-L-lysine-methylester (▽); 0.18 mM insulin+0.37 mM $N^\alpha$-deoxycholyl-L-lysine-methylester (▼); 0.18 mM insulin+27 mM $N^\alpha$-deoxycholyl-L-lysine-methylester (■); 0.18 mM insulin+37 mM $N^\alpha$-deoxycholyl-L-lysine-methylester (□).

A circular dichroism spectropolarimeter (Jasco J-715, Tokyo, Japan) was used to measure the effect of a delivery carrier on the aggregation state of insulin. Solutions containing 0.18 mM insulin and different concentration of MP-DCK (0.18-37 mM) were scanned from 300 to 250 nm at room temperature at a scanning speed of 50 nm/min using a cuvette with a pathlength of 0.1 cm. The results of the test are illustrated in FIG. 5. These results show that increasing amounts of delivery agent decrease the aggregation state of the insulin.

EXAMPLE 5

In Vivo Evaluation of Deliver Agent/Low Molecular Weight Heparin (LMWH) for Oral Formulation An oral LMWH formulation was prepared by mixing of a LMWH solution and an illustrative delivery agent solution, $N^\alpha$-deoxychoyl-L-lysine-methylester. Centaparinuxw LMWH was dissolved in PBS (10 mM, pH 7.4) containing 2% Tween® 80 to a final concentration 20 mg/ml as a stock solution. The delivery agent was dissolved in PBS (20 mg/ml). LMWH complexes were prepared by addition of a predetermined dose of delivery agent solution to LMWH solution while vortexing. LMWH complexes were then orally administered to the animals in liquid form using a gavage needle.

Figure 6:
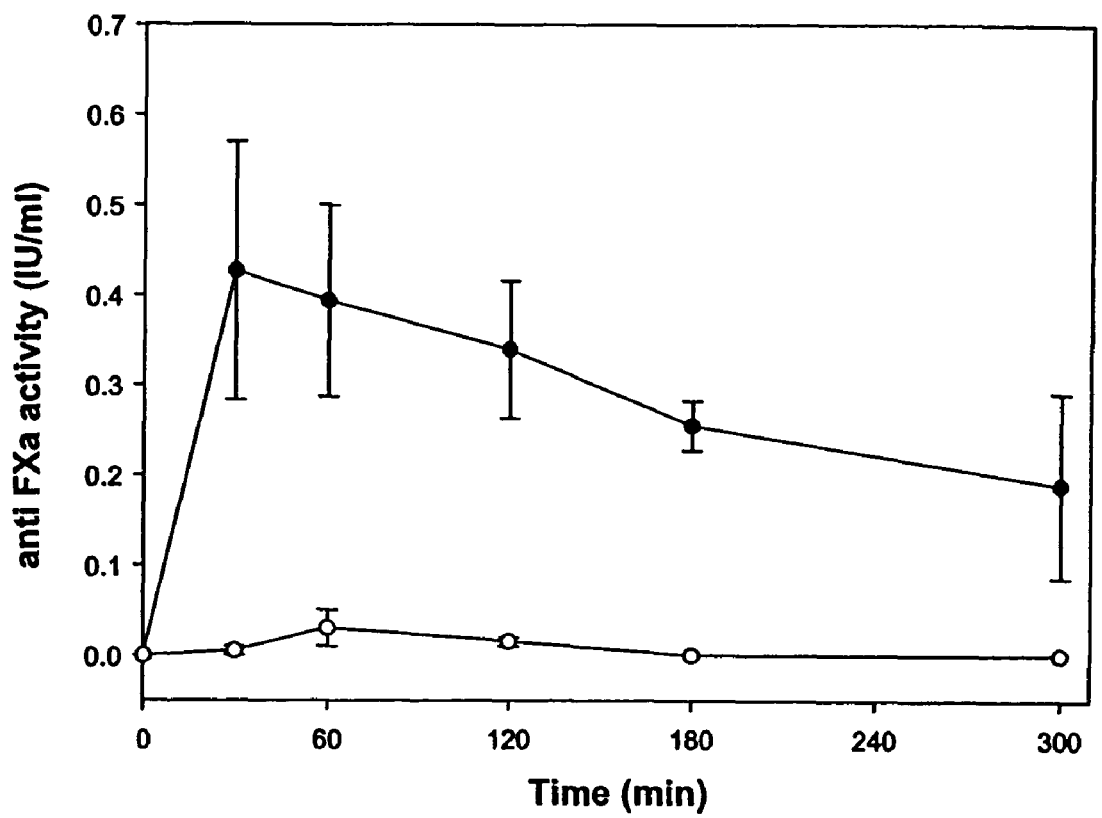
FIG. 6 shows the effect of $N^\alpha$-deoxycholyl-L-lysine-methylester on the concentration of low molecular weight heparin (LMWH) in the plasma after oral administration, as measured by antiFXa assay: 20 mg/kg LMWH (○); 20 mg/kg of LMWH+20 mg/kg of $N^\alpha$-deoxycholyl-L-lysine-methylester (●).

SD rats (a group comprised 4 rats per cage) were fasted overnight. Rats were then slightly anesthetized with diethyl ether, and the LMWH oral formulation were administered by oral gavage into the stomach. The total administered volume was 0.4 ml. Blood (450 µl) was collected from the orbital plexus and mixed with 50 µl of sodium citrate buffer. The blood samples were centrifuged at 2500 g for 20 min at 4° C. The concentration of heparin derivative in the plasma was measured by antiFXa assay. The results are illustrated in FIG. 6. These results show that co-administration of a delivery agent according to the present invention together with low molecular weight heparin results in a significant increase in antiFXa activity as compared to administration of LMWH without the delivery agent.

The invention claimed is:

1. A composition comprising a mixture of a biologically active agent and a delivery agent, wherein the delivery agent comprises (a) a hydrophobic moiety selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof and (b) $N^\alpha$-L-lysine-methylester covalently bonded to the hydrophobic moiety.

2. The composition of claim 1 wherein the composition comprises a reversible complex that is decomplexed in the blood stream after delivery to a warm-blooded animal.

3. The composition of claim 1 wherein the biologically active agent comprises insulin.

4. The composition of claim 1 wherein the hydrophobic moiety comprises deoxycholic acid.

5. The composition of claim 1 wherein the delivery agent has a molecular weight of about 400 to about 4000 daltons.

6. The composition of claim 1 further comprising one or more members selected from the group consisting of excipients, diluents, disintegrants, lubricants, plasticizers, colorants, and mixtures thereof.

7. A dosage form for delivery of a biologically active agent to a warm-blooded animal, the dosage form comprising a mixture of the biologically active agent and a delivery agent, wherein the delivery agent comprises (a) a hydrophobic moiety selected from the group consisting of bile acids, sterols, and small hydrophobic molecules having a molecular weight of less than about 500 daltons and (b) $N^\alpha$-L-lysine-methylester covalently bonded to the hydrophobic moiety; wherein the biologically active agent is selected from the group consisting of human growth hormone, recombinant human growth hormone, bovine growth hormone, porcine growth hormone, growth hormone-releasing hormone, alpha-interferon, beta-interferon, gamma-interferon, interleukin-1, interleukin-2, insulin, porcine insulin, bovine insulin, human insulin, human recombinant insulin, insulin-like growth factor (IGF), insulin-like growth factor-1 (IGF-1), glucagon-like peptide-1 (GLP-1), heparin, unfractionated heparin, heparinoids, dermatans, chondroitins, low molecular weight heparin, pentasaccharide, calcitonin, salmon calcitonin, eel calcitonin, human calcitonin, erythropoietin, atrial naturetic factor, antigens, monoclonal antibodies, somatostatin, adrenocorticotropin, gonadotropin releasing hormone, oxytocin, leutinizing-hormone-releasing-hormone, follicle stimulating hormone, glucocerebrosidase, thromboprotein, fugrastim, prostaglandins, cyclosporin, vasopressin, cromolyn sodium, sodium chromoglycate, disodium chromoglycate, vancomycin, parathyroid hormone, fragments of parathyroid hormone, desferrioxamine, and vitamins; analogs, fragments, mimetics, and polyethylene glycol-modified derivatives thereof; and mixtures thereof.

8. The dosage form of claim 7 further comprising one or more members selected from the group consisting of excipients, diluents, disintegrants, lubricants, plasticizers, colorants, and mixtures thereof.

9. The dosage form of claim 7 wherein the hydrophobic moiety comprises deoxycholic acid.

10. The dosage form of claim 7 wherein the delivery agent has a molecular weight of about 400 to about 4000 daltons.

11. The dosage form of claim 7 wherein the dosage form comprises a tablet, a capsule, a powder, a liquid, or an emulsion.

\* \* \* \* \*